United States Patent
Schuessler et al.

(10) Patent No.: US 12,290,351 B2
(45) Date of Patent: May 6, 2025

(54) MODULAR OSCILLOMETRY DEVICE WITH DYNAMIC CALIBRATION

(71) Applicant: THORASYS THORACIC MEDICAL SYSTEMS INC., Montreal (CA)

(72) Inventors: Thomas Florian Schuessler, Montreal (CA); Guy Drapeau, Montreal (CA); Lucas Posada Estefan, Montreal (CA); Geoffrey Nicholas Maksym, Dartmouth (CA)

(73) Assignee: THORASYS THORACIC MEDICAL SYSTEMS INC., Montreal (CA)

( * ) Notice: Subject to any disclaimer, the term of this patent is extended or adjusted under 35 U.S.C. 154(b) by 950 days.

(21) Appl. No.: 17/292,032

(22) PCT Filed: Nov. 11, 2019

(86) PCT No.: PCT/CA2019/051603
§ 371 (c)(1),
(2) Date: May 7, 2021

(87) PCT Pub. No.: WO2020/093176
PCT Pub. Date: May 14, 2020

(65) Prior Publication Data
US 2021/0393161 A1    Dec. 23, 2021

Related U.S. Application Data

(60) Provisional application No. 62/758,011, filed on Nov. 9, 2018.

(51) Int. Cl.
*A61B 5/087* (2006.01)
*A61B 5/097* (2006.01)

(52) U.S. Cl.
CPC .............. *A61B 5/087* (2013.01); *A61B 5/097* (2013.01); *A61B 2560/0228* (2013.01);
(Continued)

(58) Field of Classification Search
None
See application file for complete search history.

(56) References Cited

U.S. PATENT DOCUMENTS

| 7,402,139 B2 | 7/2008 | Ganshorn |
| 2009/0253994 A1 | 10/2009 | Schuessler |

(Continued)

FOREIGN PATENT DOCUMENTS

| CN | 104023633 A | 9/2014 |
| CN | 107174250 | 9/2017 |

(Continued)

OTHER PUBLICATIONS

SEFAR: "Technical information and applications for PEEK fabrics", Dec. 1, 2008 (Dec. 1, 2008).

(Continued)

*Primary Examiner* — Jay B Shah
(74) *Attorney, Agent, or Firm* — NORTON ROSE FULBRIGHT CANADA LLP

(57) ABSTRACT

A module for an oscillometry system of the type having an oscillatory flow source, the module comprises an enclosure adapted to be releasably connected to a core assembly of the oscillometry system. The enclosure defines a breathing flow pathway adapted to be in fluid communication with the oscillatory flow source. A user port is at a first end of the breathing flow pathway configured for receiving a breath of a user. A calibration file specific to the module is programmed as a function of the breathing flow pathway and configured for being used by the oscillometry system to assess breathing parameters for the user.

20 Claims, 8 Drawing Sheets

(52) U.S. Cl.
CPC ................ *A61B 2560/0443* (2013.01); *A61B 2562/0247* (2013.01); *A61B 2562/18* (2013.01)

(56) References Cited

U.S. PATENT DOCUMENTS

| | | |
|---|---|---|
| 2014/0309546 A1 | 10/2014 | Fazzi et al. |
| 2016/0038057 A1* | 2/2016 | Johnson ................ A61B 5/087 600/533 |
| 2017/0135603 A1 | 5/2017 | Hanewinkel et al. |

FOREIGN PATENT DOCUMENTS

| | | |
|---|---|---|
| EP | 0616792 B1 | 6/1998 |
| EP | 1731089 A1 | 12/2006 |
| JP | S57-122846 A | 7/1982 |
| JP | 2008-546492 A | 12/2008 |
| JP | 2013-512718 A | 4/2013 |
| JP | 2015-536787 A | 12/2015 |
| WO | 2015066562 A2 | 5/2015 |
| WO | 2016004004 A1 | 1/2016 |

OTHER PUBLICATIONS

Shackleton Claire: "Improving the clinical utility of the Forced Oscillation Technique in preschool-aged children", The University of Queensland, [Online] Jun. 21, 2018 (Jun. 21, 2018), pp. 1-294.
Osamu Nagano et al: "Bias flow rate and ventilation efficiency during adult high-frequency oscillatory ventilation: a ung model study", Intensive Care Medicine Experimental, Biomed Central Ltd, London, UK, vol. 6, No. 1, Apr. 19, 2018 (Apr. 19, 2018), pp. 1-12.

* cited by examiner

MODULAR OSCILLOMETRY DEVICE WITH DYNAMIC CALIBRATION

TECHNICAL FIELD

The present disclosure relates to devices to measure respiratory mechanics by oscillometry, also referred to as Forced Oscillation Technique (FOT).

BACKGROUND

Oscillometry, FOT, is a known method to assess lung function during normal, quiet breathing, for example in the context of asthma or chronic obstructive pulmonary disease (COPD). Unlike conventional techniques to measure lung functions such as spirometry or peak flow, oscillometry does not rely on a voluntary effort by the patient to perform a specific manoeuvre.

To obtain an oscillometry measurement, a machine-generated oscillation, typically containing one or more frequencies in the range from 5 to roughly 40 Hz, is superimposed on the patient's quiet breathing. Air flow in and out of the patient's lungs and pressure close to the airway opening are recorded using a device, and computational algorithms such as the Fourier Transform or time-frequency analysis are used to calculate a breathing parameter such as the respiratory system input impedance (Zrs) from the oscillatory component.

Ideally, the pressure and flow signals used to calculate Zrs would be recorded exactly at the interface between the device and the patient's airways. Such a patient interface could be a mouthpiece, a mask over mouth and/or nose, an endotracheal, intubation or tracheostomy tube, a laryngeal mask, just to name a few. In the example of a mouthpiece, therefore, pressure and flow would be measured exactly at the tip of the mouthpiece that is located inside the patient's mouth during normal operation. This way, the raw impedance (Z0) calculated from the original pressure and flow signals would correspond to Zrs without need for further processing or transformations.

In practice, however, further effort is required to accurately determine Zrs, for several reasons. First, the physical size of the transducers, as well as their sensitivity to the patient's body heat and/or body fluids, make it unpractical to measure pressure and flow exactly at the interface between the device and the patient, which may be situated close to or even in the patient's body. Second, patient interface components (such as mouthpieces, masks or tubes, as described above) for hygienic reasons are often disposable and separated from the sensors and the remainder of the system by bacterial/viral filters that prevent cross-contamination between patients. As a result, oscillometry systems may generally contain a significant amount of tubing, ducts, conduits, filters and/or membranes between the patient interface and the site of pressure and flow measurement. Finally, the sensitive transducers used to capture the small-amplitude oscillatory pressure and flow swings, as well as their mode of attachment to the breathing conduits, often possess manufacturing tolerances, so that every individual device may have different characteristics. Moreover, the individual characteristics may be altered as part of routine field servicing of oscillometry devices.

Another important determinant of the measurement quality is the impedance of the atmosphere port, i.e. the opening through which the patient's inspiratory and expiratory breathing airflow enters and exits the device, respectively. This port impedance must be optimally selected for each patient in order to optimize the signal-to-noise ratio of the measurement without unduly loading and/or discomforting the patient's breathing.

Consequently, the measuring systems, the pathways between the measuring systems and the patient interface and the atmosphere port possess important dynamic properties that may vary between individual devices and configurations. An individual dynamic characterization and compensation may be required in order to increase an accuracy of the determination of Zrs.

Without loss of generality, it can be stated that such a dynamic calibration may in the least contain two impedances, namely one impedance Za capturing predominantly resistive and inertive losses along the conduits between measurement site and patient interface, and a second impedance Zb predominantly capturing gas compression and wall stiffness of such conduits, as illustrated in FIG. 1.

Oscillometry systems may possess a limited measurement accuracy, especially at higher loads representing diseased and/or smaller pediatric lungs. Such inaccuracies may be a function of the issues described above, namely that the dynamic characteristics and calibrations are not sufficiently accurate or specific to the exact application and configuration at hand.

The problem described above creates a dilemma in the design of oscillometry equipment: on one hand, device configurations must be tightly controlled and individually characterized to achieve and maintain measurement accuracy; on the other hand, different applications and markets require flexible system configurations, customizations and field servicing that risk invalidating such individual calibrations and compromising measurement accuracy.

SUMMARY

It is an aim of the present disclosure is to provide a modular oscillometry device with dynamic calibration that addresses issues related to the prior art.

Therefore, in accordance with a first embodiment of the present disclosure, there is provided a module for an oscillometry system of the type having an oscillatory flow source, the module comprising: an enclosure adapted to be releasably connected to a core assembly of the oscillometry system, the enclosure defining a breathing flow pathway adapted to be in fluid communication with the oscillatory flow source, a user port at a first end of the breathing flow pathway configured for receiving a breath of a user; a calibration file specific to the module, the calibration file programmed as a function of the breathing flow pathway and configured for being used by the oscillometry system to assess breathing parameters for the user.

Further in accordance with the first embodiment, for instance, a protective element is in the breathing flow pathway.

Still further in accordance with the first embodiment, for instance, the protective element is a filter.

Still further in accordance with the first embodiment, for instance, a flow meter is in the enclosure and in fluid communication with the breathing flow pathway.

Still further in accordance with the first embodiment, for instance, the flow meter includes a pneumotachograph resistive mesh screen with a differential pressure transducer.

Still further in accordance with the first embodiment, for instance, the pneumotachograph resistive mesh screen is made of polyetheretherketone.

Still further in accordance with the first embodiment, for instance, a pressure meter (or more) may be in the enclosure and in fluid communication with the breathing flow pathway.

Still further in accordance with the first embodiment, for instance, ports of the pressure meter are located in an arcuate segment that is at most 75 degrees from either side of a center line of the user port.

Still further in accordance with the first embodiment, for instance, an atmospheric port is in the enclosure and is in fluid communication with the breathing flow pathway.

Still further in accordance with the first embodiment, for instance, the breathing flow pathway bends from an axial portion including the user portion to a radial portion including the atmospheric portion.

Still further in accordance with the first embodiment, for instance, a flow conditioning mesh may be in or adjacent to the bend of the breathing flow pathway.

Still further in accordance with the first embodiment, for instance, a flexible pipe may be connected to the enclosure and defining part of the breathing flow pathway.

Still further in accordance with the first embodiment, for instance, a bias flow source may be in fluid communication with the breathing flow pathway.

Still further in accordance with the first embodiment, for instance, a processing unit may be in the enclosure, and a non-transitory computer-readable memory communicatively coupled to the processing unit and comprising computer-readable program instructions executable by the processing unit, the calibration file being programmed into the non-transitory computer-readable memory.

Still further in accordance with the first embodiment, for instance, a modular oscillometry system comprises a core assembly having an oscillatory flow source; and the module as defined above.

Still further in accordance with the first embodiment, for instance, the core assembly has a processing module including a non-transitory computer-readable memory communicatively coupled to the processing unit and comprising computer-readable program instructions executable by the processing unit for assessing a breathing parameter of the user using the calibration file.

Still further in accordance with the first embodiment, for instance, including a user interface may be on the core assembly for displaying data.

Still further in accordance with the first embodiment, for instance, the oscillatory flow source is a piston connected to a linear actuator.

Still further in accordance with the first embodiment, for instance, the oscillatory flow source is loudspeaker.

In accordance with a second embodiment of the present disclosure, there is provided a system for calculating at least one breathing parameter comprising: a processing unit; a non-transitory computer-readable memory communicatively coupled to the processing unit and comprising computer-readable program instructions executable by the processing unit for: controlling an oscillatory flow on a breathing flow pathway of a module, receiving pressure and/or flow data from at least one breath in the breathing flow pathway of the module, obtaining a calibration file representative of dynamic properties specific to the breathing flow pathway of the module, and calculating and outputting the at least one breathing parameter using the pressure and/or flow data and the calibration file.

Further in accordance with the second embodiment, for instance, the system obtains another calibration file for another one of the module and calculates and outputs the at least one breathing parameter using the pressure and/or flow data and the other calibration file.

In accordance with a third embodiment of the present disclosure, there is provided a modular oscillometry system where individual dynamic calibrations are encapsulated with the application-specific and/or field-serviceable portions of the device, so that flexibility of reconfiguration and adaptation to new applications can be coexist with the best possible measurement accuracy in all configurations. Therefore, in accordance with the present disclosure, there is provided an oscillometry device comprising: a core assembly having an oscillatory flow source, a processing module and a user interface, and an encapsulated module releasably connected to the core assembly, the encapsulated module having a breathing flow pathway in fluid communication with the oscillatory flow source, the breathing flow pathway adapted to receive a breath of the patient, the encapsulated module including the application-specific and/or field-serviceable portions of the oscillometry device, wherein individual dynamic calibrations are encapsulated in the encapsulated module.

DETAILED DESCRIPTION

Figure 1:
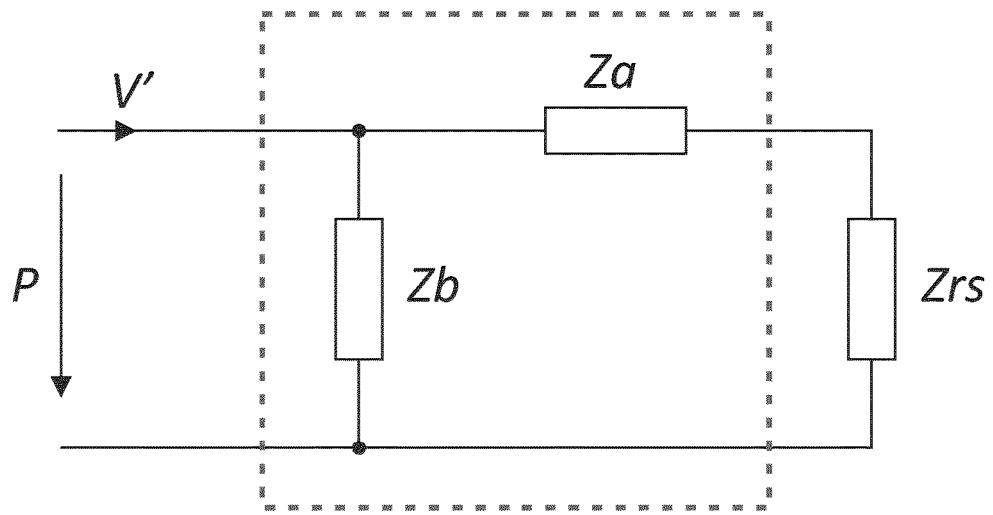
FIG. 1 is a block diagram illustrating the use of a dynamic calibration to calculate the respiratory system input impedance Zrs from a raw impedance Z0.
Figure 2:
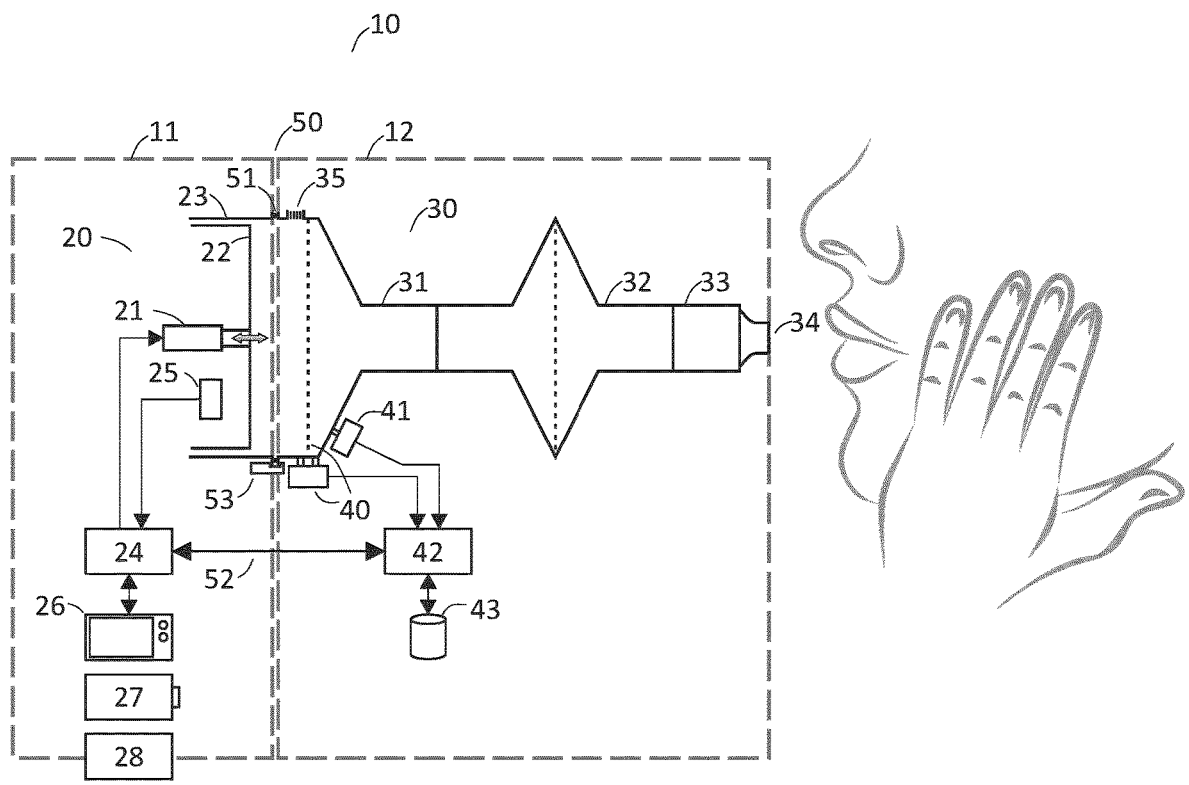
FIG. 2 is a schematic view with a block diagram of a modular oscillometry system with encapsulated dynamic calibration in accordance with an embodiment of the present disclosure.

Referring to the drawings, and more particularly to FIG. 2, there is shown, in accordance with the present disclosure, a modular oscillometry system 10 that consists of two sub-assemblies, namely a core assembly 11, and a module 12. Without loss of generality, it may be stated that the core assembly 11 may be comparatively application-independent and permanent in nature, whereas the module 12 may be more application-specific and subject to replacement from time to time, for example to reconfigure the system for a different application or patient group, or as part of regular field servicing. According to one embodiment, a same core assembly 11 may be used with different modules 12. The module 12 may be releasably detachable from the core assembly 11, such that different modules 12 may be used with the core assembly 11.

The core assembly 11 contains an oscillatory flow source 20. According to an embodiment, the oscillatory flow source 20 illustrated in FIG. 2 is a linear actuator 21 connected to a piston 22 that is moving in a housing 23. As one example among others, the oscillatory flow source 20 may be a membrane driven by a linear oscillator, a loudspeaker, a rotary fan, a pump or a valve connected to source of pressurized air, just to name a few.

The core assembly 11 may further contain a processing module 24 with all required electronics, including one or more processors with memory for data storage, communication facilities, peripherals such as A/D and D/A converters, signal amplifiers, filters and an oscillator driver. The processing module 24 may further include a non-transitory computer-readable memory communicatively coupled to the processing unit and comprising computer-readable program instructions executable by the processing unit. The core assembly 11 may also have additional sensors 25 to measure additional signals such as device orientation relative to gravity, temperature or the displacement of the piston 22, just to name a few. The core assembly 11 may further include a user interface module 26, which in itself may include indicators outputting information to the user, such as lights, displays, speakers or buzzers, just to name a few, and inputs receiving commands from the user, such as buttons, touch interfaces, pointer devices or scroll wheels, to name a few among others. The core assembly 11 may also contain an energy source 27 such as a power supply, power cord, inductive transmission element, battery or solar panel, just to name a few, and an attachment interface 28 such as a notch, clamp, bracket or screw, just to name a few, allows the system 10 to be physically supported, e.g. by attaching it to a stand, support arm, tripod, rack, bedframe, wheelchair or similar. Any one or any combination of such components may be integrated into or include a single casing or enclosure of the core assembly 11, as schematically shown by the stippled lines of 11 in FIG. 2. Alternatively, the core assembly 11 need not be in a single enclosure, as the processing unit, the user interface module 26, the energy source 27, for example, could be in a separate device, such as a portable device (e.g., tablet, reader, phone) or in a laptop, as possibilities.

The module 12 has its own enclosure (a.k.a., body, casing) separate from the enclosure of the core assembly 11. The module 12 may enclose or define a breathing flow pathway 30, or part thereof (e.g., the breathing flow pathway 30 may have parts thereof out of the enclosure), which consists of a conduit 31 to which is attached, optionally via a protective element 32 such as a bacterial/viral filter, a patient interface component 33 that is illustrated as a mouthpiece, in accordance with an embodiment. The patient interface component 33 may also be a mask covering a user's mouth and/or nose, an endotracheal, intubation or tracheostomy tube, or a laryngeal mask, just to name a few. The proximal end of the patient interface component 33 forms a patient port 34 that may represent the cut-off point from which the respiratory system impedance Zrs and/or other breathing parameter is to be measured. The expression "patient port" 34 is used herein, but also the expression "user port" 34. To clarify, the user of the system 10, i.e., the person whose respiratory system will be assessed, need not be a patient and/or may not have a medical condition or pathology, whereby the expression "patient" should be viewed as a moniker of an end of the pathway 30, and as being used on a person being tested. Moreover, the Zrs values reported must include the contributions of all respiratory system elements located downstream from the patient port 34 but no contributions of the equipment components located upstream from the patient port 34, wherein downstream and upstream are defined in the direction of inspiratory flow.

Further part of the flow pathway 30 is an atmosphere port 35 through which air enters into the conduit 31 during inspiration, and air exits from conduit 31 during expiration. As described above, the impedance of the atmosphere port 35 in the frequency range of the oscillatory waveform may be chosen to optimize the signal-to-noise ratio of the measurement while avoiding excessive patient loading. As described below, the atmosphere port 35 may be part of the core assembly 11, the pathway 30 being define concurrently by the core assembly 11 and the module 12.

In an embodiment, a flow meter 40 (a.k.a., flowmeter) may be in fluid communication with the conduit 31 to measure the airflow into and out of the patient's airway opening. The flow meter 40 is illustrated as a pneumotachograph resistive mesh screen with a differential pressure transducer. Other types of flow meters may be used, such as a honeycomb, ultrasonic, pitot, variable orifice or venturi pneumotachograph, just to name a few.

Since expired air is conditioned to body temperature and humidity, e.g., 37 degrees Celsius and 100% relative humidity, condensation may occur on parts of the flow pathway 30 that are naturally cooler, e.g. at ambient room temperature. This can affect some types of flow meter 40, for example those that are of mesh or honeycomb type. Such flow meters may rely on the linearity and stability of the airflow resistance of their structures, and condensation may alter the expected linearity and airflow resistance of these structures. Such flow meters may be heated to a temperature close to the expired air temperature to prevent condensation from occurring. In an embodiment, flow meter components produced from hydrophobic materials such as polyetheretherketone (PEEK) may be used, as they may reduce the accumulation of condensation on the flowmeter resistive mesh.

The module 12 may also include a pressure meter 41 in fluid communication with the conduit 13, to measure the pressure in the conduit 31. In an embodiment, the pressure meter 41 is located on the side of the flow meter 40 that is towards the patient, though other arrangements are possible. The flow meter 40 and pressure meter 41 are connected to a processing module 42 that may include one or more processors, memory for data storage, peripherals such as A/D and D/A converters, signal amplifiers and filters. The processing module 42 may or may not further include a non-transitory computer-readable memory communicatively coupled to the processing unit and comprising computer-readable program instructions executable by the processing unit. In another embodiment, the signals from the components of the module 12, such as the flow meter 40 and/or pressure meter 41 may be processed by the processing module 24 in the core assembly 11. Connected to or contained in the processing module 42 is a repository 43 or like database in which module-specific information such as identifiers, electronic data sheets and, importantly, dynamic calibration data (e.g., calibration file) for this module 12 are stored in non-volatile memory (e.g., flash memory). The repository 43 or a portion of it may also be contained in the core assembly 11 or another location, e.g. an online "cloud" repository.

The module 12 may be connected to the core assembly 11 through a module interface 50. A seal 51 or like sealing or airproof arrangement may be present between the oscillator 20 and the conduit 31, so that air flow can pass through the flow pathway 30, i.e. from the atmosphere port 35 to the patient port 34 and vice versa, without significant losses. The module interface 50 may also include a communication link 52 that allows the processing module 24 on the core assembly 11 to communicate with the processing module 42 on the module 12 (if present). The communication link 52 may be achieved via wired connection, wireless connections such as Bluetooth®, optical encoding, magnetic encoding or RFID tags, to name just a few solution among others. The interface 50 may include means 53 to physically secure the module 12 to the core assembly 11, which may include one or more screw, clamp, bayonet or magnetic attachment, snap fit connectors, just to name a few.

When the module 12 is mounted to the core assembly 11, the oscillometry system 10 has all components that are needed to generate the oscillation, record the pressure and flow measurements. The measurements may be processed by the system 10, or remotely therefrom, to compute Zrs and/or other related breathing parameters.

In one embodiment, the processing module 24 includes means of communication to transmit such recordings to an external computational device such as a computer, tablet, smart phone, telemedicine server or central database, just to name a few. The processing module 24 in this case may also communicate with the processing module 42 (if present) to retrieve the module-specific information and calibration factors contained in the repository 43 or associated to the module 12. The module-specific information and calibration factors may then be included with the measurement data, so that the analysis module running on the external computational device has access to all information required to compute Zrs and/or other related breathing parameters.

In a similar embodiment, both the processing module 24 and the processing module 42 have means of communication to directly communicate with an external computational device (but not necessarily with each other), in a manner that allows the external computational device to synchronize and align data and metadata from both sources as needed to accurately compute Zrs and/or other related breathing parameters.

In another embodiment, the processing modules 24 and 42 may have the processing capacity to directly calculate Zrs using the calibration factors contained in repository 43. If a user interface module 26 is present in the system 10, the results may be displayed in situ. Concurrently, the system 10 may transfer intermediate results and/or final outcomes to an external computational device or database as described above, for storage, visualization and further analysis.

As required, the module 12 contained in the modular oscillometry system 10 may be replaced, either as part of a field service or to adapt the system for a different application. In the latter case, a reconfiguration may be required, for example, to adapt a system previously used for adult subjects to children or infants, where different pathway sizes and measurement sensitivities may be needed, and/or to decontaminate a module 12 used in a highly contagious patient group, and/or to switch to a different type of bacterial/viral filter 32 for sourcing reasons, and/or to optimize the patient comfort, just to name a few. The processing module 24, the processing module 42 and/or and the external computational system, as the case may be, have access to the information unique to the module 12 (such as contained in repository 43). Therefore, the processing module 24, the processing module 42 and/or and the external computational system can adjust their assessment by using the dynamic calibration data specific to the module 12 in order to calculate Zrs from the reconfigured system 10, without need for user intervention or adjustment and/or in situ calibration. Stated differently, the calibration data/file specific to the module 12 may be a fingerprint of the module 12, i.e., how the breathing flow pathway 30 personally affects the flow by its own unique geometry and characteristics (e.g., surface friction, location of components, etc, that affect the flow for each pathway 30). The calibration file may be obtained through bench testing of the modules 12 so as to have individual calibration files programmed for each module 12.

Figure 3:
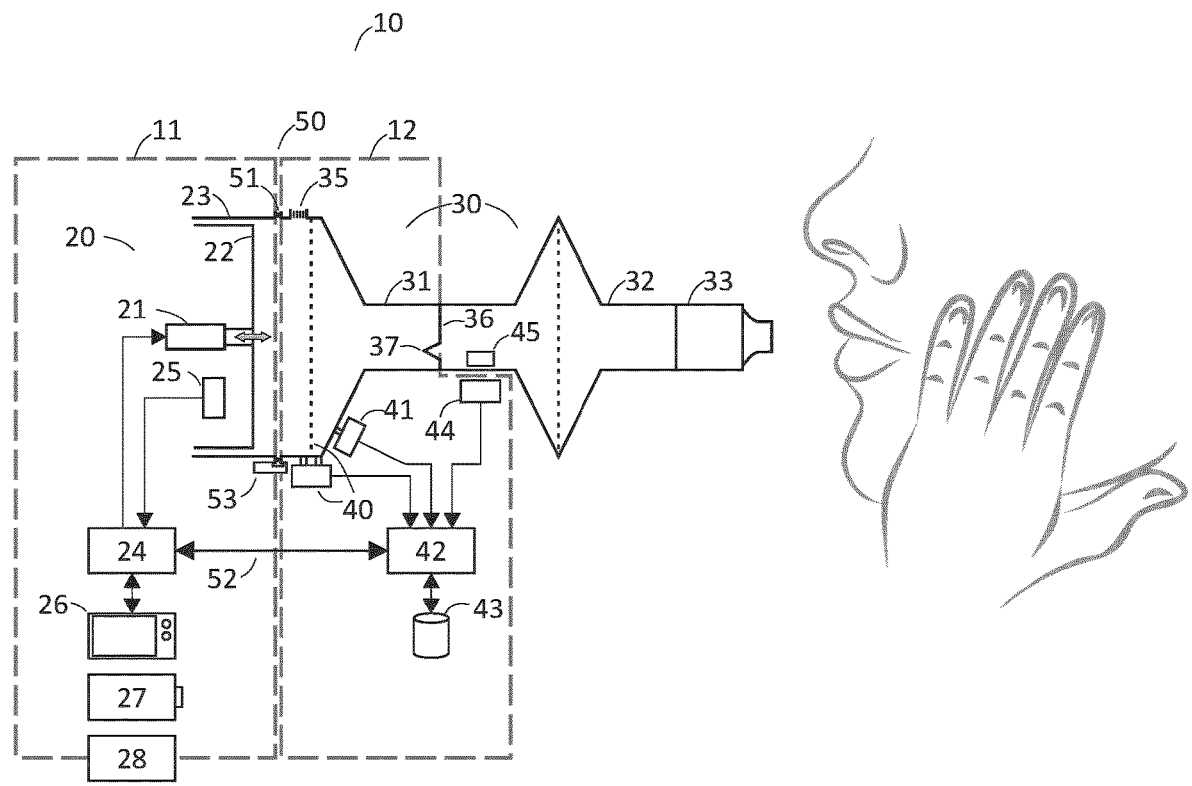
FIG. 3 is a schematic view with a block diagram of a modular oscillometry system with encapsulated dynamic calibration in accordance with another embodiment of the present disclosure.
Figure 4:
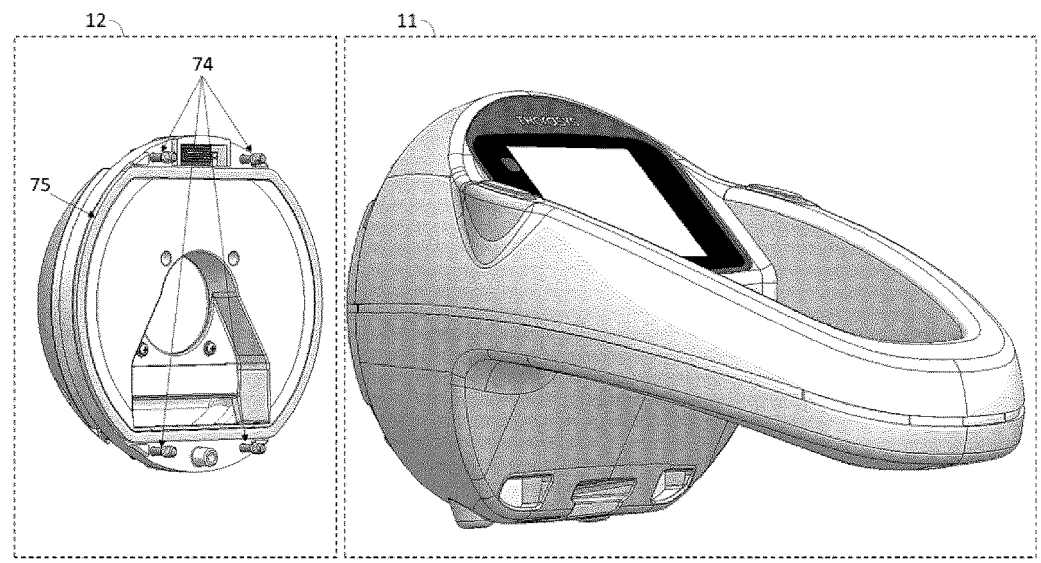
FIG. 4 is a perspective view of an exemplary interface between a module and core assembly of the modular oscillometry system in accordance with another embodiment of the present disclosure.

In another embodiment shown in FIG. 3, the protective element 32 and the patient interface component 33 may be physically separate from and externally attached, e.g., releasably detachable, to the module 12 through a port 36 at the patient end of conduit 31. This may be useful, for example, if the protective element 32 and the patient interface component 33 are implemented as single-use disposable supplies, which may be required or desired for sanitary reasons. Moreover, and without loss of generality, the protective element 32 and the patient interface component 33 may be manufactured as a single part, for example as a bacterial/viral filter with integrated mouthpiece, or as a face mask with integrated bacterial/viral filter, just to name a few. The protective element 32 and the patient interface component 33 may be releasably connected to the enclosure of the module 12 by any appropriate arrangement, such as threaded engagement, interference fit, and/or seals, etc.

For the embodiment shown in FIG. 3, the dynamic calibration data (e.g., contained in repository 43) represents the dynamic properties of the entire flow pathway 30, including the user-replaceable components, i.e. the protective element 32 and the patient interface component 33. Accordingly, a dedicated module 12 containing individual dynamic calibration factors specific to the type of user-replaceable components, may be used to enhance accuracy for each allowed combination of the protective element 32 and the patient interface component 33, if dynamic properties are deemed to vary with the user-replaceable components. Information contained in the repository 43, for example, and communicated via the link 52 may be used to inform the user of the required type of components, for example via display on the user interface module 26 or via the external computational device, just to name a few. Moreover, to ensure that only the correct disposables are used, a unique key feature 37 may be included in port 36. The unique key feature 37 may provide a mechanical interference to block non-compatible disposables. Alternately or additionally, a detector 44 connected to the processing module 42 may be used to read a type-identifier from a tag 45 located on the protective element 32 in order to ensure that a disposable is present and only permissible disposables are used. In an embodiment, repository 43 may contain multiple calibration files for different compatible types of disposables, and the type information obtained from detector 44 and tag 45 may be used to automatically select from repository 43 the correct calibration file for the permissible disposable that has been attached by the user.

A more detailed drawing of a similar embodiment is shown in Erreur! Source du renvoi introuvable. In this embodiment, the interface between the core assembly 11 and the module 12 is shown as a compression mechanism 74 consisting of fasteners such as screws, bolts, or the like. The tightening of the fasteners presses the module 12 against the core assembly 11. There may result an airtight coupling between the application-specific and/or field-serviceable portion module 12 with the core assembly 11 by evenly compressing for example a compliant, reusable sealant component 75. The sealant component 75 may be any appropriate type of seal, such as a closed cell foam. The use of a compliant material allows for the use of relative low-force/low-pressure fastening mechanisms such as a low number of screws, manual latches, thumb screws, magnets, to name a few. In an embodiment, the sealant component 75 lies in a plane, with a direction of compression having a vector being normal to the plane of the sealant component 75. In another embodiment, no sealant component 75 is present, the system relying instead on complementary surfaces or features.

Figure 5:
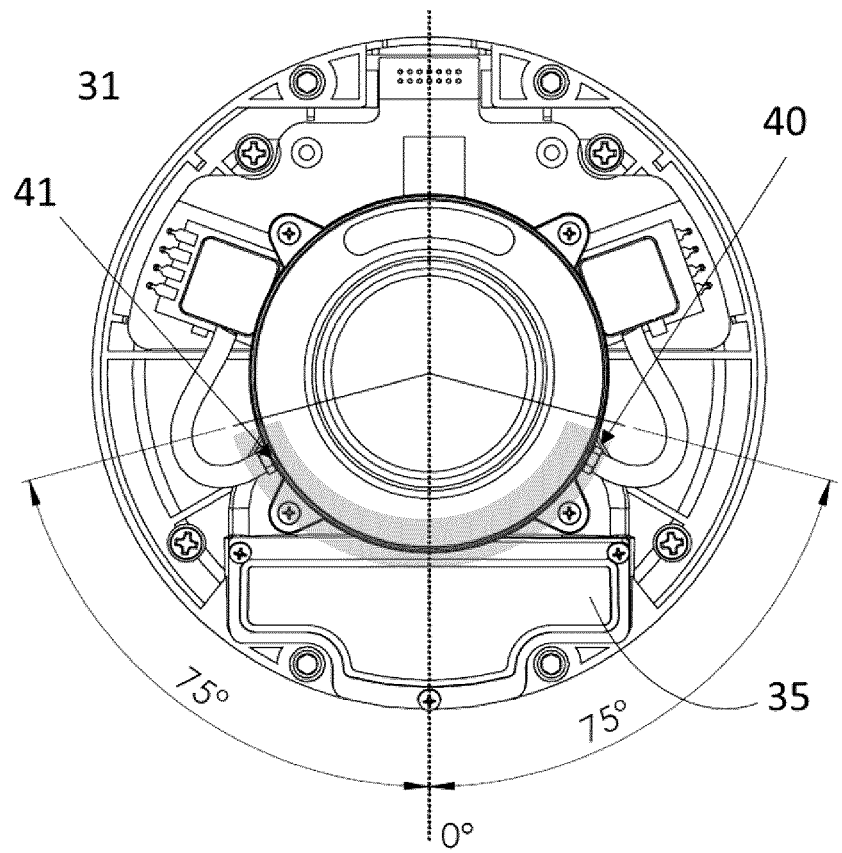
FIG. 5 is a perspective view of a relative angular position of the flow ports and pressure port in the module in accordance with another embodiment of the present disclosure.
Figure 6:
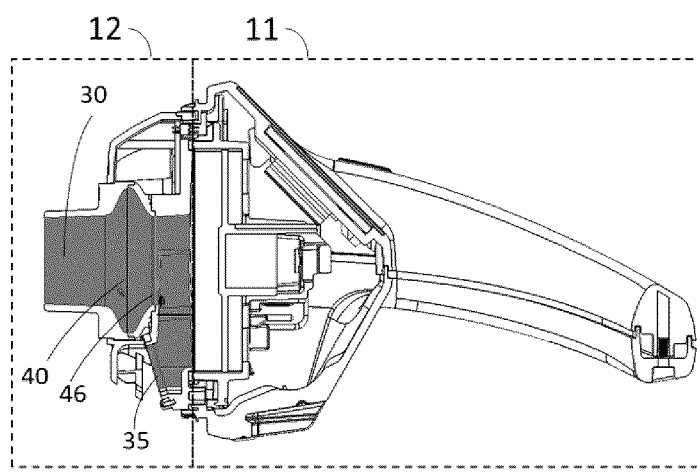
FIG. 6 is a perspective view of an exemplary geometry of a flow pathway including a conditioning mesh in accordance with another embodiment of the present disclosure.
Figure 7:
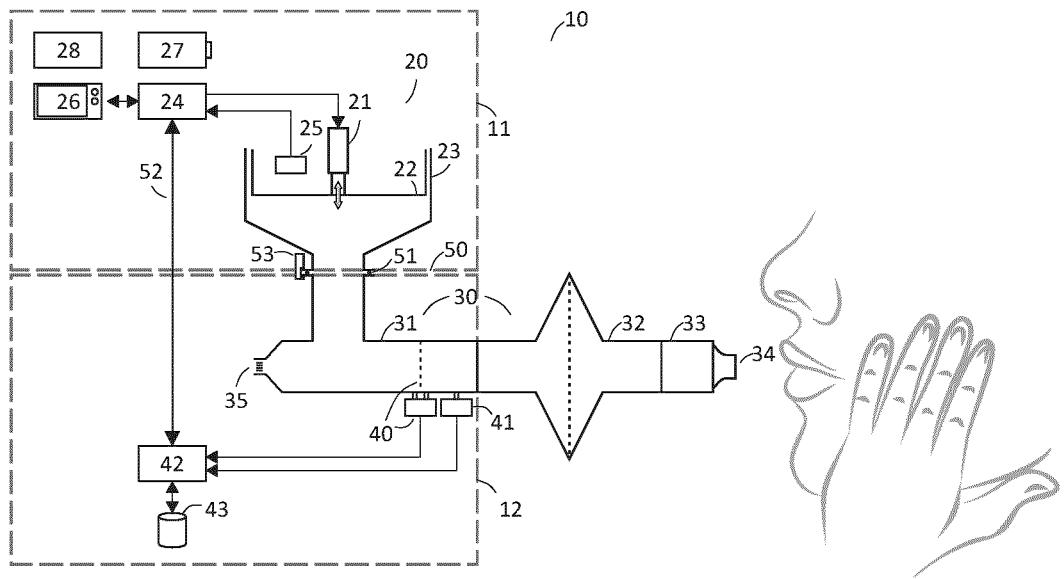
FIG. 7 is a schematic view of a modular oscillometry system with encapsulated dynamic calibration in accordance with yet another embodiment of the present disclosure.
Figure 8:
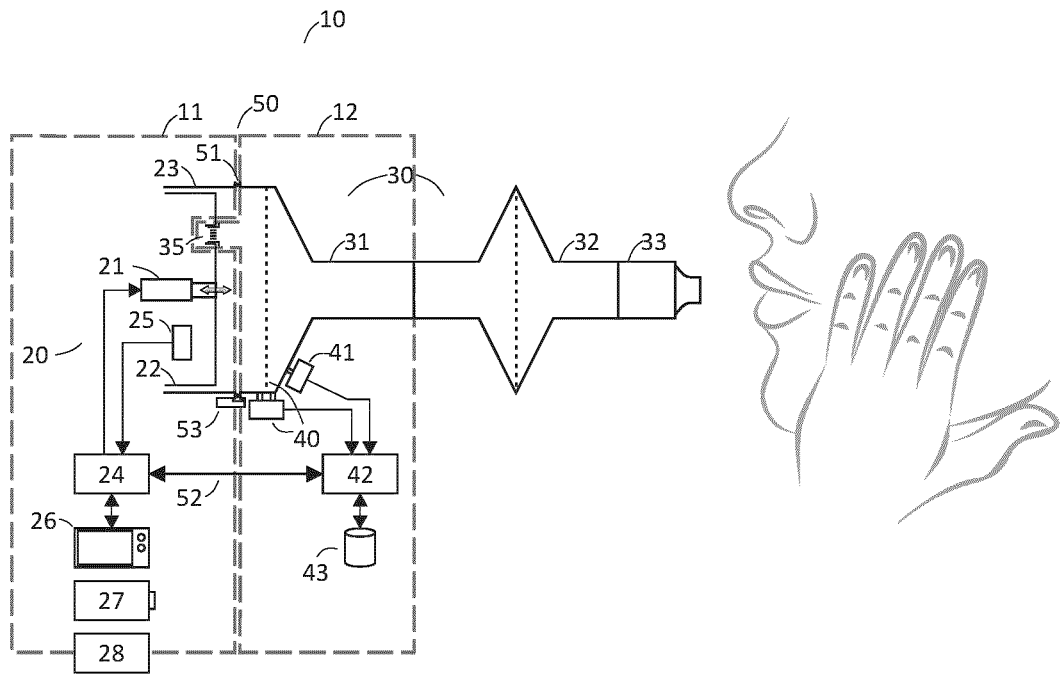
FIG. 8 is a schematic view of a modular oscillometry system with encapsulated dynamic calibration in accordance with yet another embodiment of the present disclosure.

In accordance with another embodiment, as shown in FIGS. 5 and 6, the atmosphere port 35 may be oriented in a generally radial direction relative to the axis of the patient port 34 and the flow meter 40. Stated differently, instead of having the pathway 30 being a straight flow-through channel (as in FIGS. 7 and 8, also in accordance with the present disclosure), the pathway 30 may curve toward the atmosphere port 35. The pathway 30 may have a straight portion at the patient port 34, with a radial portion away from the patient port 34. The expression "radial portion" is used to indicate that the pathway curves or bends away from a central axis of the straight portion, in a radial direction. In an embodiment, the curve or being is gradual, for instance like a candy-cane, or part of a candy-cane. This has the advantage that the patient's expired air is not directed towards a nearby operator, for example when the system 10 is handheld by the operator. This results in a non-straight complex flow pathway 30. In such a configuration, the ports of the pressure meter 41 may be located in an arcuate segment that is at most 75 degrees from either side of the center line through the atmosphere port 35 and patient port 34, on the side of the atmosphere port 35. In such an arrangement, pressure is measured in parts of the flow pathway 30 where airflow turbulence is least likely to occur. Other arrangements are however contemplated. When the type of flow meter 40 used involves measurement of a differential pressure, which is the case for example with a mesh pneumotachograph, the same considerations may apply to the placement of the differential pressure ports of the flow meter 40. In a curved flow pathway 30, the pressure may be sampled at different positions in the flow stream, choosing positions along the pathway 30 that sample pressure drop at the mean flow or higher or below. In an embodiment, the average pressure may be suited, but a related position for average pressure may not necessarily be in the center of a curved path. The location of the pressure ports may consequently be based on accurate reproduction of theoretical test load impedance, experimentally determined in a test bed. Accordingly, there may result the configuration shown in FIG. 5, i.e., with the ports of the pressure meter 41 located in an arcuate segment that is 75 degrees from either side of the center line through the atmosphere port 35 and patient port 34, on the side of the atmosphere port 35. The calibration file may take the location into consideration, for instance by adding some compensation for other effect on estimates of impedance, such as turbulence.

In an embodiment, the measurement accuracy of a non-straight flow pathway configuration may be enhanced as illustrated in Erreur! Source du renvoi introuvable, by placing an additional flow conditioning mesh 46 between the flow meter 40 and the zone where flow transitions from the axial to the radial direction in the flow pathway 30 bend. This flow conditioning mesh 46 may reduce turbulence, to keep the flow laminar at the site of the flow meter 40.

The radial orientation of the atmosphere port 35 as discussed for the above embodiment is merely one of many possible configurations. In the alternate embodiment shown in Erreur! Source du renvoi introuvable., the atmosphere port 35 is arranged in the same axis as the patient port 34 and the flow meter 40, and the interface 50 towards the oscillator 20 is arranged in a side port that is positioned transversally or orthogonally to that axis. In yet another embodiment shown in Erreur! Source du renvoi introuvable., the atmosphere port 35 is implemented as a plug insert into piston 22, so that the resistive element providing the termination impedance to atmosphere moves with the piston face when the oscillator 20 is active ("vibrating mesh" configuration).

Figure 9:
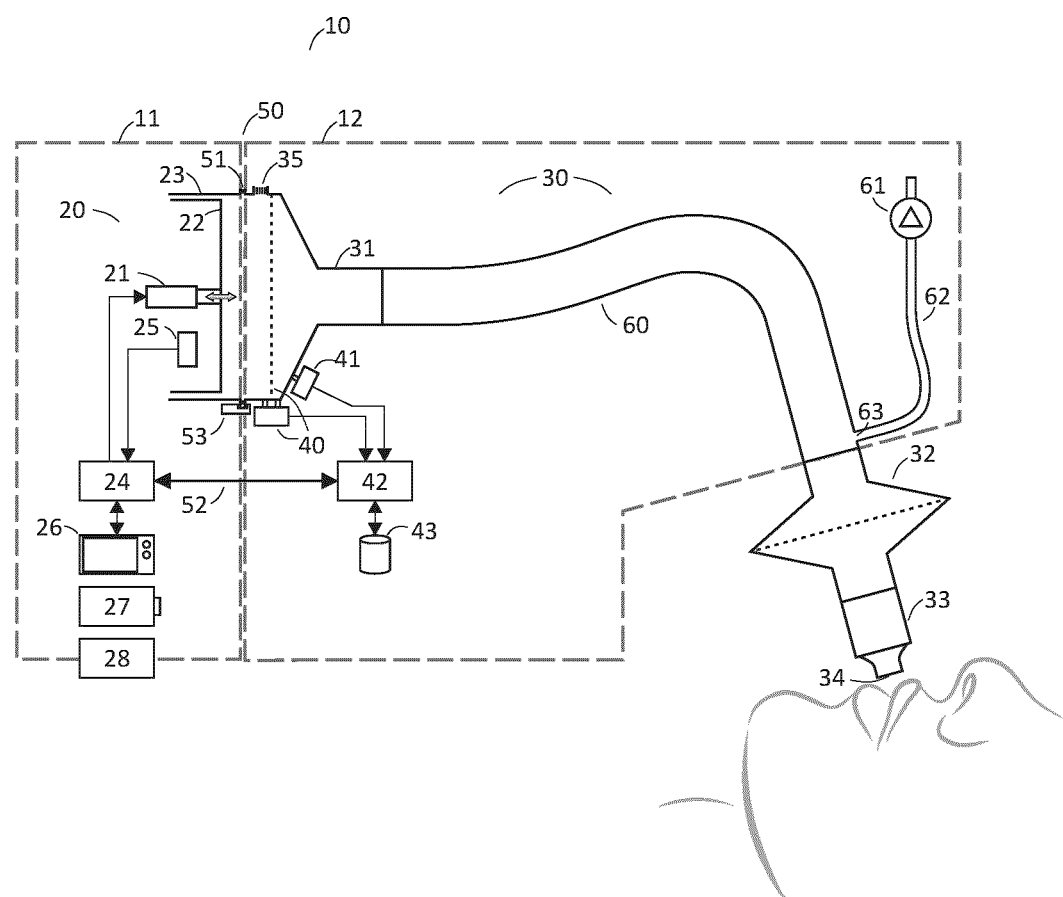
FIG. 9 is a schematic view of a modular oscillometry system with encapsulated dynamic calibration in accordance with yet another embodiment of the present disclosure.

In another embodiment shown in FIG. 9, a flexible tube 60 may be inserted into the flow pathway 30 between the conduit 31 and the protective element 32 (or alternately, but not illustrated in the figures, between the protective element 32 and the patient interface component 33) in order to allow flexible placement of the system 10 in relation to the patient and vice versa. This may be useful to measure patients who are physically immobilized and/or unable to get close to the system 10, such as physically handicapped patients seated in a wheelchair, supine patients in a bed, or children or infants lying in a crib, just to name a few, as well as to obtain measurements from patients who may be easily disturbed by the vibration of the oscillator, such as sleeping subjects and particularly sleeping infants.

In some cases, the addition of the flexible tube 60 may increase the dead space within the flow pathway 30 beyond permissible levels. In such cases, a bias flow source 61 may be included in the system 10 and connected to a side port 63 via a pathway 62 that must have a sufficiently high impedance to shunt the oscillatory flow produced by oscillator 20. The bias flow rate must be sufficient to wash out the volume contained in the flow pathway 30 between the atmosphere port 35 and the bias flow port 63, so that this volume no longer contributes to the ventilatory equipment dead space.

Figure 10:
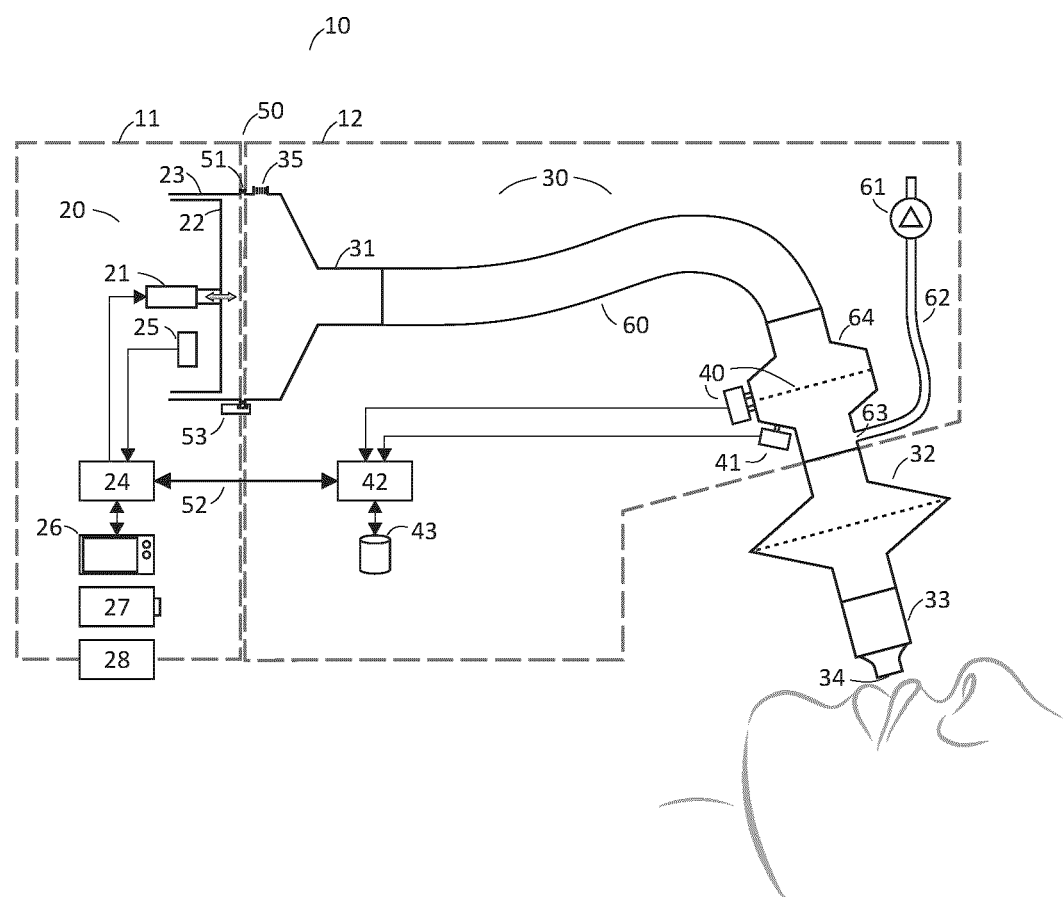
FIG. 10 is a schematic view of a modular oscillometry system with encapsulated dynamic calibration in accordance with yet another embodiment of the present disclosure.

In another embodiment shown in FIG. 10, the flow meter 40 and pressure meter 41 are implemented as part of a measurement head 64 that is inserted between the flexible tube 60 and the protective element 32. This approach may in some applications help optimize the signal-to-noise ratio. The placement of the bias flow source 61 and the bias flow port 63 shown in FIGS. 9 and 10 is merely exemplary. For example, the bias flow port could also be integrated into the protective element 32 or into the patient interface component 33, or situated between the protective element 32 and the patient interface component 33. Similarly, the bias flow source 61 may be a pump contained in the module 12, a pump contained in the core assembly 11.

Figure 11:
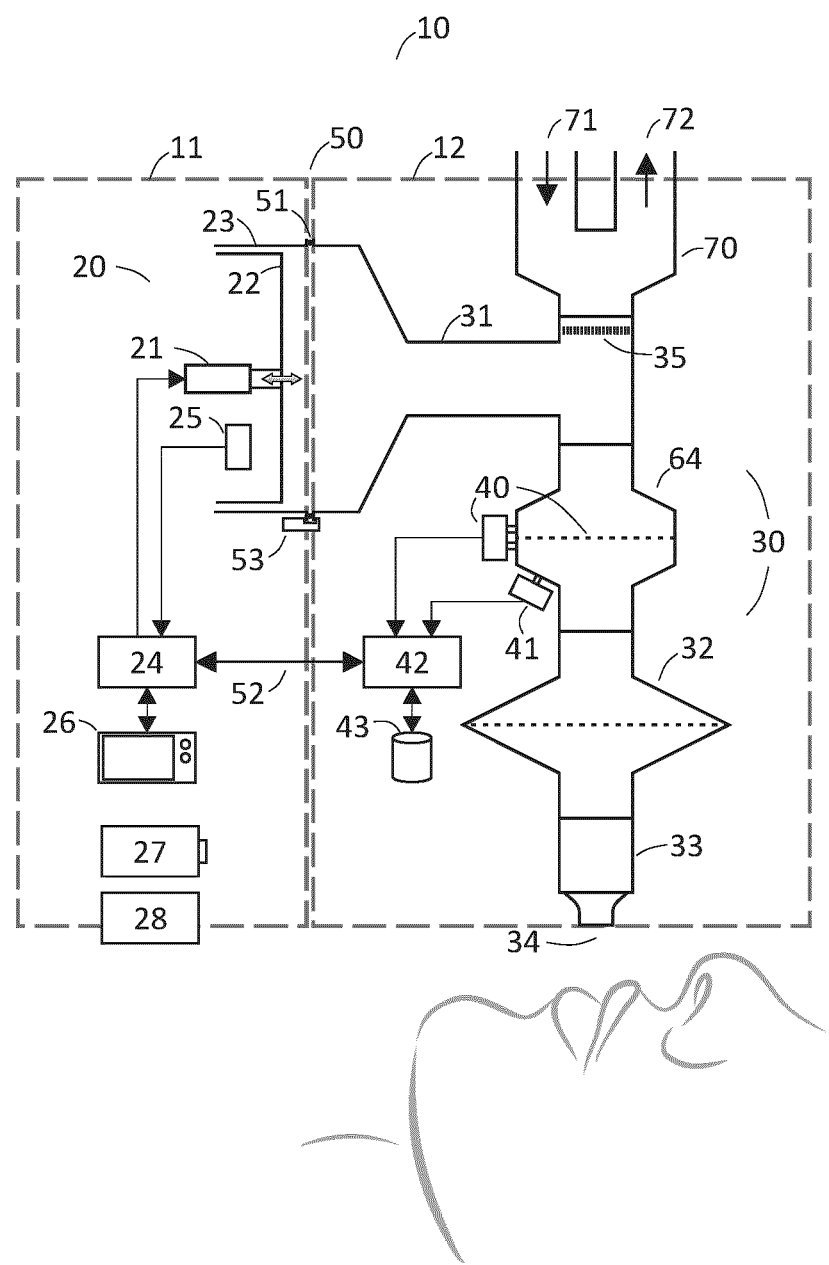
FIG. 11 is a schematic view of a modular oscillometry system with encapsulated dynamic calibration in accordance with yet another embodiment of the present disclosure.
Figure 12:
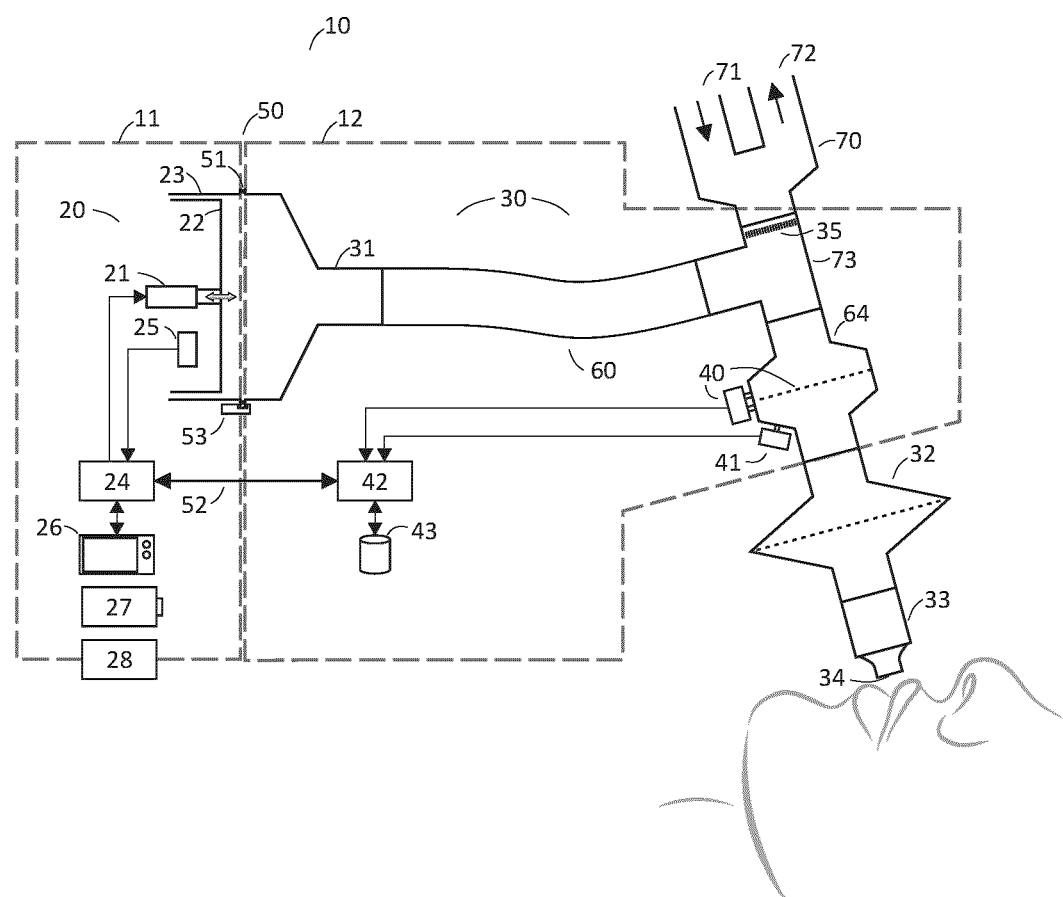
FIG. 12 is a schematic view of a modular oscillometry system with encapsulated dynamic calibration in accordance with yet another embodiment of the present disclosure.

Another embodiment shown in FIG. 11 may serve to obtain oscillometry measurements in patients receiving mechanical ventilation. In this embodiment, the conduit 31 and the atmosphere port 35 contained therein are shaped such that a standard ventilator Y-piece 70 can be connected to the atmosphere port 35. The inspiratory pathway 71 and the expiratory pathway 72 may then be connected to a typical mechanical ventilator in order to provide ventilatory support to the patient. In such an embodiment, the impedance of the atmosphere port 35 is optimized to increase the fraction of the oscillatory flow generated by the oscillator 20 reaches the patient's lungs and the signal-to-noise ratio of the measurement is optimized while avoiding excessive loading of the breathing circuit.

If, again, the application requires the oscillator to be physically separated from the patient, for example to avoid undue vibration of the ventilator tubing, a flexible tube 60 may again be attached to the conduit 31, as shown in FIG. 9. A manifold 73 with three ports, such as a T-piece or a Y-piece, is attached to the other side of the flexible tube 60. Attached to the second port of that manifold is a measurement head 64, as previously detailed, to which is further connected the protective element 32 or into the patient interface component 33, and ultimately the patient. The third and final port of the manifold 73 is the atmosphere port 35, which as in the previous embodiment is connected to the ventilator tubing.

In all embodiments, calibration factors specific to the module 12 at hand are embedded in the repository 43, or available to the system 10 for calculation, so that measurement accuracy is enhanced after exchanging a module 12. For instance, the system 10 may upload or obtain the calibration file specific to the module 12 (e.g., using a unique identifier, etc) for performing the assessment. Moreover, additional sensors or user inputs such as buttons may be included with a given type of module to enable ergonomic operation.

The module 12 may be generally described as a module for an oscillometry system of the type having an oscillatory flow source. The module 12 has an enclosure adapted to be releasably connected to the core assembly 11 of the oscillometry system 10, the enclosure defining a breathing flow pathway 30 adapted to be in fluid communication with the oscillatory flow source 20. A user port 34 at a first end of the breathing flow pathway 30 may be configured for receiving a breath of a user. To assess breathing parameters for the user, a calibration file specific to the module 12 is programmed as a function of the breathing flow pathway and configured for being used by the oscillometry system 10 in the assessment.

The system 10 may be generally described as being for calculating one or more breathing parameters, including impedance Zrs described above. The system 10 may include one or more processing units, such as 24 and/or 42, with a non-transitory computer-readable memory communicatively coupled to the processing unit and comprising computer-readable program instructions executable by the processing unit for: controlling an oscillatory flow on a breathing flow pathway of a module, receiving pressure and/or flow data from at least one breath in the breathing flow pathway of the module, obtaining a calibration file representative of dynamic properties specific to the breathing flow pathway of the module, and calculating and outputting the at least one breathing parameter using the pressure and/or flow data and the calibration file. The system 10 may obtain another calibration file for another one of the module and calculates and outputs the at least one breathing parameter using the pressure and/or flow data and the other calibration file.

The invention claimed is:

1. A module for an oscillometry system of the type having an oscillatory flow source, the module comprising:
an enclosure adapted to be releasably connected to a core assembly of the oscillometry system, the enclosure including a breathing flow pathway adapted to be in fluid communication with the oscillatory flow source, a user port at a first end of the breathing flow pathway configured for receiving a breath of a user;
a calibration file specific to the module, the calibration file programmed as a function of the breathing flow pathway and configured for being used by the oscillometry system to assess breathing parameters for the user.

2. The module according to claim 1, wherein a protective element is in the breathing flow pathway.

3. The module according to claim 2, wherein the protective element is a filter.

4. The module according to claim 1, wherein a flow meter is in the enclosure and in fluid communication with the breathing flow pathway.

5. The module according to claim 4, wherein the flow meter includes a pneumotachograph resistive mesh screen with a differential pressure transducer.

6. The module according to claim 5, wherein the pneumotachograph resistive mesh screen is made of polyetheretherketone.

7. The module according to claim 1, further comprising a pressure meter in the enclosure and in fluid communication with the breathing flow pathway.

8. The module according to claim 7, wherein the pressure meter includes ports located in an arcuate segment that is at most 75 degrees from either side of a center line of the user port.

9. The module according to claim 1, wherein an atmospheric port is in the enclosure and is in fluid communication with the breathing flow pathway.

10. The module according to claim 9, wherein the breathing flow pathway bends from an axial portion including the user portion to a radial portion including the atmospheric portion.

11. The module according to claim 10, further comprising a flow conditioning mesh in or adjacent the bend of the breathing flow pathway.

12. The module according to claim 1, including a flexible pipe connected to the enclosure and defining part of the breathing flow pathway.

13. The module according to claim 12, including a bias flow source in fluid communication with the breathing flow pathway.

14. The module according to claim 1, including a processing unit in the enclosure, and a non-transitory computer-readable memory communicatively coupled to the processing unit and comprising computer-readable program instructions executable by the processing unit, the calibration file being programmed into the non-transitory computer-readable memory.

15. A modular oscillometry system comprising:
a core assembly having an oscillatory flow source; and
the module as defined in claim 1.

16. The modular oscillometry system according to claim 15, wherein the core assembly has a processing module including a non-transitory computer-readable memory communicatively coupled to the processing unit and comprising computer-readable program instructions executable by the processing unit for assessing a breathing parameter of the user using the calibration file.

17. The modular oscillometry system according to claim 15, including a user interface on the core assembly for displaying data.

18. The modular oscillometry system according to claim 15, wherein the oscillatory flow source is a piston connected to a linear actuator.

19. The modular oscillometry system according to claim 15, wherein the oscillatory flow source is loudspeaker.

20. A system for calculating at least one breathing parameter comprising:
a processing unit;
a non-transitory computer-readable memory communicatively coupled to the processing unit and comprising computer-readable program instructions executable by the processing unit for:
controlling an oscillatory flow on a breathing flow pathway of a module,
receiving pressure and/or flow data from at least one breath in the breathing flow pathway of the module,
obtaining a calibration file representative of dynamic properties specific to the breathing flow pathway of the module, and
calculating and outputting the at least one breathing parameter using the pressure and/or flow data and the calibration file.

\* \* \* \* \*